United States Patent [19]
Guskey et al.

[11] Patent Number: 5,976,514
[45] Date of Patent: Nov. 2, 1999

[54] LOW-IRRITATION ANTIPERSPIRANT AND DEODORANT COMPOSITIONS CONTAINING A VOLATILE, NONPOLAR HYDROCARBON LIQUID

[75] Inventors: Gerald John Guskey, Montgomery; Curtis Bobby Motley; Christine Marie Putman, both of West Chester; Philip Andrew Sawin, Cincinnati, all of Ohio

[73] Assignee: Procter & Gamble Company, Cincinnati, Ohio

[21] Appl. No.: 09/197,146

[22] Filed: Nov. 20, 1998

[51] Int. Cl.$^6$ ............... A61K 7/32; A61K 7/34; A61K 7/38; A61K 31/74; A61K 7/00
[52] U.S. Cl. ............... 424/65; 424/66; 424/68; 424/78.02; 424/400; 424/401
[58] Field of Search ............... 424/65, 66, 68, 424/400, 401, 78.02

[56] References Cited

U.S. PATENT DOCUMENTS

| | | | |
|---|---|---|---|
| 4,263,274 | 4/1981 | Kulkarni et al. | 424/46 |
| 4,265,878 | 5/1981 | Keil | 424/68 |
| 4,446,051 | 5/1984 | Berthod et al. | 252/309 |
| 4,724,139 | 2/1988 | Palinczar | 424/66 |
| 5,585,104 | 12/1996 | Ha et al. | 424/401 |
| 5,607,980 | 3/1997 | McAtee et al. | 514/476 |
| 5,665,364 | 9/1997 | McAtee et al. | 424/401 |
| 5,716,625 | 2/1998 | Hahn et al. | 424/401 |

FOREIGN PATENT DOCUMENTS 0 500 941 B1  8/1995  European Pat. Off. .

*Primary Examiner*—Shelley A. Dodson
*Attorney, Agent, or Firm*—William J. Winter; Tara M. Rosnell; Michael E. Hilton

[57] ABSTRACT

Disclosed are topical compositions which comprise from about 0.01% to about 60% by weight of an antiperspirant and/or deodorant active; from about 1% to about 60% by weight of a volatile, nonpolar hydrocarbon liquid having a solubility parameter of less than about 7.5 $(cal/cm^3)^{0.5}$ and a vapor pressure as measured at 25° C. of from about 0.01 mmHg to about 6.0 mmHg; and from about 1% to about 60% by weight of a skin irritation-mitigating material having a vapor pressure equal to or less than that of the volatile, nonpolar hydrocarbon liquid, preferably a silicone-containing liquid; wherein the weight ratio of the volatile, nonpolar hydrocarbon liquid to the mitigating material is from about 5:1 to about 1:50. It has been found that the volatile, nonpolar hydrocarbon liquid as defined herein can cause skin irritation when used in an antiperspirant or deodorant composition, even when used at relatively low concentrations, but that the skin irritation can be reduced or eliminated by the addition of a skin irritation-mitigating material, provided the material has the requisite vapor pressure and weight ratio relative to the volatile, nonpolar hydrocarbon liquid.

34 Claims, No Drawings

LOW-IRRITATION ANTIPERSPIRANT AND DEODORANT COMPOSITIONS CONTAINING A VOLATILE, NONPOLAR HYDROCARBON LIQUID

TECHNICAL FIELD

The present invention relates to low-irritation antiperspirant and deodorant compositions which comprise a volatile, nonpolar hydrocarbon liquid and a skin irritation-mitigating material. The mitigating material reduces or eliminates skin irritation associated with the topical application of the volatile, nonpolar hydrocarbon liquid from an antiperspirant or deodorant composition.

BACKGROUND OF THE INVENTION

There are many types of topical antiperspirant and deodorant products that are commercially available or otherwise known in the antiperspirant and deodorant art. Most of these products are formulated as aerosol or pump sprays, roll-on liquids, creams, emulsions, gels, gel-solids, or other solid or semi-solid stick formulations, and comprise a deodorant (e.g., triclosan) and/or astringent material (e.g. zirconium and/or aluminum salts) incorporated into a suitable carrier. These products are designed to provide effective perspiration and/or odor control while also being cosmetically acceptable during and after application onto the axillary area or other areas of the skin.

Within this product group, antiperspirant and deodorant products containing volatile silicone fluids have become especially popular among consumers. These products can be aqueous or anhydrous and can contain up to 80% by weight of a volatile silicone fluid such as cyclopentasiloxane. The volatile silicone provides the composition with dry skin feel during application, and because of its volatility, it evaporates quickly after application leaving the applied surface feeling smooth and dry with no residual white marks. Volatile silicones are expensive, however, and add substantially to the cost of the finished antiperspirant and deodorant products.

To control the relatively high formulation cost associated with the use of volatile silicone fluids, volatile, nonpolar hydrocarbon liquids have been used in place of some or all of the volatile silicones. Volatile nonpolar hydrocarbon liquids are typically less expensive than the volatile silicones, and like the volatile silicones, also help provide the composition with dry feel during and after application to the skin. Examples of compositions containing volatile, nonpolar hydrocarbon liquids are described in U.S. Pat. No. 4,724,139, issued Feb. 9, 1988 to Palinczar and U.S. Pat. No. 4,265,878, issued May 5, 1981 to Keil.

It has now been found, however, that antiperspirant and deodorant compositions containing volatile, nonpolar hydrocarbon liquids can be very irritating to the skin even when used at relatively low concentrations. It is believed that this irritation problem has not previously been disclosed in the literature as being associated with the use of these materials in deodorant and antiperspirant products. For example, U.S. Pat. No. 4,724,139 (Palinczar) teaches that volatile silicones can be replaced with volatile, nonpolar hydrocarbon liquids in antiperspirant sticks since the two materials have similar characteristics, including good cosmetics, high volatility, and low skin irritation. It has now been found, however, that these volatile, nonpolar hydrocarbon liquids when placed in either an antiperspirant or deodorant composition can cause significant skin irritation upon and after topical application even when the concentration of such liquids in the finished product is relatively low.

It has also now been found that antiperspirant and deodorant compositions containing a volatile, nonpolar hydrocarbon liquid can be formulated so as to minimize or eliminate the skin irritation caused by the volatile, nonpolar hydrocarbon liquid. It has been found that this skin irritation can be can be minimized or eliminated by the concurrent use of select solvents that act as skin irritation-mitigating materials (mitigating materials), provided that the weight ratio of the volatile, nonpolar hydrocarbon liquid to the mitigating material is from about 5:1 to about 1:50. The select solvents must have a vapor pressure equal to or less than that of the volatile, nonpolar hydrocarbon liquid. Highly preferred skin irritation-mitigating materials are nonvolatile silicone fluids.

It is therefore an object of the present invention to provide an antiperspirant or deodorant composition which contains a volatile, nonpolar hydrocarbon liquid, and which causes little or no skin irritation when applied topically to the axilla or other area of the skin. It is a further object of the present invention to provide such a composition which also contains a skin irritation-mitigating material, preferably a nonvolatile silicone fluid, to help minimize or eliminate the development of skin irritation after topical application.

SUMMARY OF THE INVENTION

The present invention is directed to antiperspirant and deodorant compositions which comprise from about 0.01% to about 60% by weight of an antiperspirant and/or deodorant active; from about 1% to about 60% by weight of a volatile, nonpolar hydrocarbon liquid having a solubility parameter of less than about 7.5 $(cal/cm^3)^{0.5}$ and a vapor pressure as measured at 25° C. of from about 0.01 mmHg to about 6.0 mmHg; and from about 1% to about 60% by weight of a mitigating material having a vapor pressure equal to or less than the vapor pressure of the volatile, nonpolar hydrocarbon liquid selected for use in the composition, wherein the weight ratio of the volatile, nonpolar hydrocarbon liquid to the mitigating material is from about 5:1 to about 1:50.

It has been found that the volatile, nonpolar hydrocarbon liquid as defined herein can cause skin irritation when applied topically from an antiperspirant or deodorant composition, but that the skin irritation can be reduced or eliminated by the addition of select amounts of mitigating materials as defined herein. The mitigating materials are preferably a nonvolatile, nonpolar hydrocarbon emollient and/or a nonvolatile silicone material, preferably a nonvolatile silicone fluid, provided that they are formulated at the select weight ratios and vapor pressures as described herein.

DETAILED DESCRIPTION OF THE INVENTION

The antiperspirant and deodorant compositions of the present invention comprise as essential elements an 1) antiperspirant and/or deodorant active, 2) a volatile, nonpolar hydrocarbon liquid as defined herein, and 3) a skin irritation-mitigating material at a defined weight ratio and vapor pressure relative to that of the volatile, nonpolar hydrocarbon liquid.

The term "volatile" as used herein, unless otherwise specified, refers to those materials that are liquid under ambient conditions and have a vapor pressure as measured at 25° C. of at least about 0.01 mmHg, typically from about 0.0 mmHg to about 6.0 mmHg, Conversely, the term "nonvolatile" as used herein, unless otherwise specified, refers to those materials which are not volatile as that term is defined herein. Such "nonvolatile" materials will typically be in the form of a liquid, semi-solid or solid, and have no measurable vapor pressure as measured at 25° C.

The term "anhydrous" as used herein refers to preferred embodiments of the compositions of the present invention, and means that these preferred embodiments are substantially free of added water. From a formulation standpoint, this means such preferred embodiments contain less than about 5%, more preferably less than about 3%, even more preferably less than about 1%, most preferably zero percent, by weight of free or added water, other than the water of hydration typically associated with the particulate antiperspirant active.

The term "ambient conditions" as used herein refers to surrounding conditions at about one atmosphere of pressure (1 atm), at about 50% relative humidity, and at about 25° C., unless otherwise specified. All values, amounts and measurements described herein are obtained under ambient conditions unless otherwise specified.

The term "nonpolar" as used herein refers to those materials that have a solubility parameter of less than about 7.5 $(cal/cm^3)^{0.5}$, typically from about 5.0 to about 7.5 $(cal/cm^3)^{0.5}$. Such materials will typically be silicone-containing materials or organic materials that contain few if any functional groups.

The antiperspirant and deodorant compositions of the present invention, including corresponding methods of the present invention, can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

The essential elements of the antiperspirant and deodorant composition of the present invention, including the essential elements of the corresponding methods application, are described in greater detail hereinafter.

1. Antiperspirant Active

The compositions of the present invention include those embodiments intended for use as antiperspirant compositions and which comprise an antiperspirant active suitable for application to human skin. The active may be dissolved in the selected solvent, or dispersed throughout the composition as unsolubilized or partially unsolubilized solids. The concentration of antiperspirant active in the composition should be sufficient to provide the desired perspiration wetness and/or odor control from the antiperspirant formulation selected.

These antiperspirant embodiments of the present invention preferably comprise antiperspirant active at concentrations of from about 0.01% to about 60%, more preferably from about 5% to about 35%, even more preferably from about 7% to about 26% by weight of the composition. These weight percentages are calculated on an anhydrous metal salt basis exclusive of water and any complexing agents such as glycine, glycine salts, or other complexing agents. The antiperspirant active as formulated in the composition are preferably in the form of dispersed solids having a preferred average particle size or diameter of less than about 100 μm, preferably less than about 50 μm. Also preferred are dispersed solid particulates having an average particle size or diameter of less than about 1 μm, even more preferably from less than about 0.4 μm, and most preferably less than about 0.2 μm.

The antiperspirant active may be solubilized or partially solubilized in the aqueous or anhydrous antiperspirant compositions of the present invention. Anhydrous antiperspirant compositions are preferred. The concentration of solubilized active in the composition preferably ranges from about 0.5% to about 35%, more preferably from about 0.5% to about 25%, even more preferably from about 1% to about 17%, and even more preferably from about 6% to about 17%, by weight of the composition. These weight percentages are calculated on an anhydrous metal salt basis exclusive of water and any complexing agents such as glycine, glycine salts, or other complexing agents. The active may be solubilized in the antiperspirant or deodorant composition with the help of additional solvents or co-solvents which are known or otherwise effective for solubilizing antiperspirant active, and which are compatible with the selected components of the antiperspirant composition or which otherwise do not unduly impair product performance.

The antiperspirant active for use in the antiperspirant embodiments of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant embodiments include those which conform to the formula:

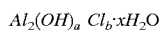

$Al_2(OH)_a Cl_b \cdot xH_2O$ wherein a is from about 2 to about 5; the sum of a and b is about 6; x is from about 1 to about 6; and wherein a, b, and x may have non-integer values. Particularly preferred are the aluminum chlorohydroxides referred to as "⅚ basic chlorohydroxide", wherein a=5, and "⅔ basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant embodiments include those which conform to the formula:

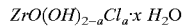

$ZrO(OH)_{2-a}Cl_a \cdot x H_2O$ wherein a is from about 1.1 to about 2.0; x is from about 1 to about 8; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

The antiperspirant embodiments of the present invention can also be formulated to comprise other dispersed solids or other materials in addition to or in place of the antiperspirant active. Such other dispersed solids or other materials include any material known or otherwise suitable for topical application to human skin, including deodorant actives and/or perfumes described hereinafter. The compositions of the present invention can also be formulated as cosmetic or topical compositions which contain no antiperspirant or other active material, particulate or otherwise.

II. Deodorant Active

The composition of the present invention includes deodorant embodiments which contain a deodorant active, perfume or combination thereof, at concentrations ranging from about 0.01% to about 60%, preferably from about 0.01% to about 20%, more preferably from about 0.01% to about 10%, even more preferably from about 0.1% to about 0.5%, by weight of the composition. These deodorant actives and perfumes include any known or otherwise safe and effective deodorant active or perfume suitable for topical application to human skin.

Deodorant actives suitable for use in the deodorant embodiments of the present invention include any topical material that is known for or is otherwise effective in preventing or eliminating malodor associated with perspiration. These deodorant actives are typically antimicrobial agents (e.g., bacteriocides, fungicides), malodor-absorbing materials, or combinations thereof.

Preferred deodorant actives are antimicrobial agents, non-limiting examples of which include acetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, phenoxyethanol, and combinations thereof.

Preferred deodorant actives are triclosan, triclocarban and combinations thereof, wherein the preferred concentration of either triclosan or triclocarban ranges from about 0.01% to about 1.0%, more preferably from about 0.1% to about 0.5%, even more preferably from about 0.1% to 0.3%, by weight of the composition, and wherein the total concentration of triclosan and triclocarban when used together in a composition ranges from about 0.01% to about 2.0%, more preferably from about 0.2% to about 1.0%, even more preferably from about 0.2% to about 0.6%, by weight of the composition.

Other deodorant actives include odor-absorbing materials such as carbonate and bicarbonate salts, including alkali metal carbonates and bicarbonates, ammonium and tetraalkylammonium. Preferred are sodium and potassium salts of such odor-absorbing materials. Still other deodorant actives include the antiperspirant actives described hereinbefore.

Perfumes suitable for use in the deodorant embodiments of the present invention include any topical material that is known for or is otherwise effective in masking malodor associated with perspiration, or which otherwise provides the composition with the desired perfumed aroma. These include any perfume or perfume chemical, including pro-perfumes and deo-perfumes, suitable for topical application to the skin.

The amount or concentration of the perfume in the deodorant embodiments should be effective to provide the desired aroma characteristics or to mask malodor, wherein the malodor is inherently associated with the composition itself or is associated with malodor development from human perspiration.

Perfumes are made by those skilled in the art in a wide variety of fragrances and strengths. Typical perfumes and fragrances are described in Arctander, Perfume and Flavour Chemicals (Aroma Chemicals), Vol. I and II (1969); and Arctander, Perfume and Flavour Materials of Natural Origin (1960). U.S. Pat. No. 4,322,308 and U.S. Pat. No. 4,304,679, both incorporated herein by reference, disclose perfume or fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as coumarin and β-naphthyl methyl ether); esters (such as diethyl phthalate, phenylethyl phenylacetate, non-anolide-1:4). Perfumes also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in perfumes herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methylionone, and amyl-cyclohexanone and mixtures of these components.

Other suitable perfumes are those which mask or help to mask odors associated with perspiration (hereinafter referred to as odor masking perfumes), some non-limiting examples of which are described in U.S. Pat. No. 5,554,588, U.S. Pat. No. 4,278,658, U.S. Pat. No. 5,501,805, and EP Patent Application 684 037 A1, all of which are incorporated herein by reference in their entirety. Preferred odor masking perfumes are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The perfume for use herein may also contain solubilizers, diluents, or solvents which are well known in the art. Such materials are described in Arctander, Perfume and Flavour Chemicals (Aroma Chemicals), Vol. I and II (1969). These materials typically include small amounts of dipropylene glycol, diethylene glycol, $C_1$–$C_6$ alcohols, and/or benzyl alcohol.

III. Volatile, Nonpolar Hydrocarbon Liquid

The antiperspirant or deodorant compositions of the present invention comprise a volatile, nonpolar hydrocarbon liquid at a concentration of from about 1% to about 60%, preferably from about 10% to about 40%, more preferably from 20% to about 40%, by weight of the composition.

The term "volatile" as used in this context refers to the volatile, nonpolar hydrocarbon liquid and means that such materials are liquid under ambient conditions and have a vapor pressure as measured at 25° C. of at least about 0.01 mmHg, preferably from about 2.0 mmHg to about 6.0 mmHg, more preferably from about 0.01 mmHg to about 2.0 mmHg, and preferably an average boiling point at one atmosphere of pressure (1 atm) of less than 250° C.

The term "nonpolar" as used in this context refers to the volatile, nonpolar hydrocarbon liquid and means that such materials have a solubility parameter of less than about 7.5 $(cal/cm^3)^{0.5}$, most typically about 5.0 $(cal/cm^3)^{0.5}$ to less than about 7.5 $(cal/cm^3)^{0.5}$. These volatile, nonpolar hydrocarbon liquids preferably contain only hydrogen and carbon and therefore preferably contain no functional groups.

Solubility parameters as used to characterize the volatile, nonpolar hydrocarbon liquids and any other nonpolar materials described herein are determined by methods well known in the chemical arts for establishing the relative polar character of a solvent or other material. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

The nonpolar, volatile hydrocarbon liquid for use in the composition of the present invention is preferably a liquid paraffin and/or isoparaffin having the requisite volatility and nonpolar character. The nonpolar, volatile hydrocarbon liquids can have a cyclic, branched and/or chain configuration, and can be saturated or unsaturated, preferably saturated.

Preferred volatile, nonpolar hydrocarbon liquids are branched chain hydrocarbons having the requisite volatility and solubility parameter, and which have from about 6 to about 40 carbon atoms, preferably from about 6 to about 20 carbon atoms. These preferred hydrocarbon liquids will most typically be formulated as a combination of two or more of the above-described branched chain hydrocarbons, wherein the combination of two or more hydrocarbons have different molecular weights, number of carbon atoms, and/or chain configurations. Specific nonlimiting examples of such combinations include the isoparaffins available from Exxon Chemical Company, Baytown, Tex. U.S.A, sold as Isopar M (C13–C14 Isoparaffin), Isopar C (C7–C8 Isoparaffin), Isopar E (C8–C9 Isoparaffin), Isopar G (C10–11 Isoparaffin), Isopar L (C11–C13 Isoparaffin), Isopar H (C11–C12 Isoparaffin), and combinations thereof. Other nonlimiting examples of suitable branched chain hydrocarbons include Permethyl 99A (C12, isododecane), Permethyl 101A (C16, isohexadecane), Permethyl 102A (C20, isoeicosane), and combinations thereof. The Permethyl series are available from Presperse, Inc., South Plainfield, N.J., U.S.A. Other nonlimiting examples of suitable branched chain hydrocarbons include petroleum distallates such as those available from Phillips Chemical as Soltrol 130, Soltrol 150, Soltrol 170, and those available from Shell as Shell Sol-70, -71, and -2033.

Still other suitable isoparaffins include C9–C11 Isoparaffin, C9–C13 Isoparaffin, C9–C14 Isoparaffin, C10–C13 Isoparaffin, C12–C14 Isoparaffin, C13–C16 Isoparaffin, C14–C18 Isoparaffin, and hydrogenated polyisobutene available from Amoco as the Panalane Series and from Fanning Corporation as the Fancor P series.

Nonlimiting examples of other volatile, nonpolar hydrocarbon liquids suitable for use in the antiperspirant and deodorant compositions include paraffins such as dodecane, octane, decane and combinations thereof, and the Norpar series of paraffins available from Exxon Chemical Company such as Norpar-12, -13, and -15 and the Neosolve series of paraffins available from Shell. Yet another example includes C11–C15 alkanes/cycloalkanes, such as those available from Exxon as Exxsol D80.

IV. Skin Irritation-Mitigating Material

The antiperspirant and deodorant compositions of the present invention comprise a skin irritation-mitigating material (also referred to herein as "mitigating material"), wherein the weight ratio of the volatile, nonpolar hydrocarbon liquid defined hereinbefore to the mitigating material is from about 5:1 to about 1:50, preferably from about 4:1 to about 1:10, more preferably from about 3:1 to about 1:5, most preferably from about 2:1 to about 1:1.

The mitigating material for use in the compositions of the present invention include any material effective in reducing skin irritation caused by the volatile, nonpolar hydrocarbon liquid component of the composition, wherein the skin irritation reduction is determined in accordance with the skin irritation methodology described herein To be effective, it has been found that these mitigating materials must also have a vapor pressure equal to or less than, preferably less than, the vapor pressure of the volatile, nonpolar hydrocarbon liquid in the composition (as measured at 25° C.). It has also been found that the most effective of these mitigating materials are nonvolatile silicone fluids.

It has been found that the volatile, nonpolar hydrocarbon liquids as defined herein cause skin irritation even when used at relatively low concentrations of from about 1% to about 60% by weight of an antiperspirant or deodorant composition. It has also been found that the mitigating materials as defined herein provide the composition of the present invention with the desired skin irritation mitigation, provided that it is incorporated into the composition at the requisite vapor pressure and weight ratios relative to the selected volatile, nonpolar hydrocarbon liquid.

The mitigating material component of the antiperspirant and deodorant compositions of the present invention may comprise one or more mitigating materials which individually or collectively are at a concentration of from about 1% to about 60%, preferably from about 5% to about 30%, more preferably from about 5% to about 10%, by weight of the composition. Any known or otherwise effective irritation-mitigating material can be used herein, provided that the mitigating material is formulated into the composition at the selected weight ratios defined above. It has been found that among these known or otherwise effective mitigating materials, nonvolatile silicone fluids are especially effective in reducing or eliminating skin irritation caused by the use of low concentrations of volatile, nonpolar hydrocarbon liquids.

The mitigating materials can also be characterized as those materials that effectively reduce skin irritation from an antiperspirant or deodorant composition when evaluated according to the 7-day cumulative skin irritation patch test described hereinafter. Skin irritation reduction is provided by a mitigating material when the mitigating composition shows a reduced LS mean irritation grade as compared to similar formulas where the mitigating material is replaced in the composition with water for aqueous compositions or cyclopentasiloxane for anhydrous compositions.

Preferred mitigating materials are nonvolatile-silicone containing materials. The nonvolatile silicone-containing materials may be in the form of solids or liquids, preferably liquids, under ambient conditions. Preferred nonvolatile silicone-containing materials are nonvolatile silicone liquids, preferably having a viscosity as measured at 25° C. of at least 5 centistokes, more preferably from about 10 centistokes to about 1000 centistokes, more preferably from about 10 centistokes to about 100 centistokes, even more preferably from about 30 centistokes to about 80 centistokes. Other suitable but less preferred silicones include silicone solids (e.g., silicone waxes) and silicone viscous fluids (e.g., silicone gums).

Nonlimiting examples of suitable silicone-containing mitigating materials for use herein include polyalkylsiloxanes, polyalkyarylsiloxanes, polyalkyl silanol siloxanes (e.g., dimethiconols) and polyethersiloxane copolymers, many examples of which are well known in the cosmetic and antiperspirant/deodorant arts, some of which are described in 1 Cosmetics, Science and Technology 27–104 (M. Balsam and E. Sagarin ed. 1972); and U.S. Pat. No. 4,202,879, issued to Shelton on May 13, 1980, which descriptions are incorporated herein by reference.

Linear, nonvolatile polydimethylsiloxane fluids are the preferred silicone-containing material for use in the antiperspirant and deodorant compositions of the present invention. Examples of such preferred silicone-containing fluids include Dow Coming 200, Rhodorsil Oils 70047 available from Rhone-Poulenc, Masil SF Fluid available from Mazer, Dow Coming 225; SF-96 and SF-1214, SF-1236 and CF-1251 Silicone Fluids (available from G. E. Silicones); Viscasil and gums such as GE SE (available from General Electric Co.); and Silicone L-45, Silicone L530, Silicone L-531 (available from Union Carbide), and Siloxane F-221 and Silicone Fluid SWS-101 (available from SWS Silicones).

It has also been found that polyalkyl silanol siloxanes (e.g., dimethiconols such as DC1401; DC2-9023; DC4-2797; YF3800; GE88017; and blends thereof) are especially effective when used in antiperspirant compositions containing relatively polar gelling agents. These relatively polar gelling agents are described hereinafter and are those gelling agents that contain at least one highly polar functionality such as a carboxylic acid or amide functionality. It has been found that these silanol siloxanes provide a more stable composition than other silicone-containing materials when used in combination with the relatively polar gelling agents, and also provide skin irritation-mitigation benefits when also used in combination with the volatile, nonpolar hydrocarbon liquid as defined herein. Preferred are polyalkylsilanol siloxanes having about 0.1% to about 5.0% silanol content, preferably from about 0.5% to about 5.0% silanol content, and a viscosity of from about 20 centistokes to about 1000 centistokes, preferably from about 20 centistokes to about 100 centistokes.

Other nonlimiting examples of suitable silicone-containing mitigating materials include silicone polyethers or silicone glycols (such as dimethicone copolyol or dimethiconol); silicone alkyl-linked polyethers (such as Goldschmidt EM-90 cetyl dimethicone copolyol or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, hydroxyl, vinyl, alkoxy, arylalkyl, aryl, phenyl, styryl, polyethers, esters, carboxylics; alkylmethyl siloxanes or silicone waxes (such as hexyl, octyl, decyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as GE SS4267, GE SS4230 and Shiseido/Shin-etsu, e.g. Japanese Patent Publication JP86143760 or from Walker Chem. 6MBH (described in EP722970); alkoxysiloxanes; alkoxysilanes; methicones; and combinations thereof.

Nonlimiting examples of other suitable silicone-containing mitigating materials include those available from Dow Coming: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-190 Fluid (Dimethicone Copolyol); DC-193 Fluid (Dimethicone Copolyol); DC-5200 Fluid (Laurylmethicone Copolyol); DC-6603 Polymer Powder; linear volatile dimethicones; DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-580 Wax (Stearoxytrimethylsilane [and] Stearyl Alcohol); DC-1-3563 (Dimethiconal); DC-X2-1286 (Dimethiconol); DC-X2-1146A (Cylcomethicone [and] Dimethiconol); DC-8820 Fluid (Amino functionalized); DC Q5-0158A wax (stearoxytrimethylsilane); DC-Q2-8220 (Trimethylsilylamodimethicone); DC-7224 (Trimethylsilylamodimethicone); DC-X2-1318 Fluid (Cyclomethicone [and] Vinyldimethicone); DC-QFI-3593A fluid (Trimethylsiloxysilicate); behenoxy dimnethicone; bisphenyl hexa methicone; C24–C28 alkyl methicone; C30–C45 alkyl methicone; cetyl dimethicone; dimethicone gums; dimethicone copolyol acetate; dimethicone copolyol butyl ether; dimethicone copolyol methyl ether; diphenyl dimethicone; stearoxy dimethicone; stearoxy methicone/dimethicone copolymer; stearyl methicone; triphenyl trimethicone; and combinations thereof.

Other nonlimiting examples of suitable silicone-containing mitigating materials include those available from General Electric: GE SF-1023 (Dimethyl-Diphenyl-Siloxane); GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1328; GE SF-1188 (Dimethicone copolyol); GE SF-1188A (Silicone polyether copolymer); GE SF-1288 (silicone polyether copolymer, dimethyl-methyl 3-hydroxypropyl ethoxylated); GE SF-1318 (Methylester Siloxane); GE SF-1328 (silicone surfactant, dimethyl-methyl 3-hydroxypropyl ethoxylated-propoxylated); GE SF-1550 (methylphenyl siloxane, hexamethyl-3-phenyl-3-[[trimethylsilyl]oxy]trisiloxane); GE SF-1632 (silicone wax); GE SS-4267 (Dimethicone [and] Trimethylsiloxysilicate), and combinations thereof.

Other nonlimiting examples of suitable silicone-containing mitigating materials include those available from Goldschmidt: Abil EM-90 (silicone emulsifier); Abil EM-97 (polyether siloxane); Abil Waxes such as Abil B 88 series and Abil Wax 9810 (silicone wax or C24-28 methicone); Abil Wax 2434 (Stearoxy Dimethicone); Abil Wax 9800D (Stearyl Dimethicone); Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone Copolymers) and combinations thereof.

Other nonlimiting examples of suitable silicone-containing mitigating materials include those available as Masil 756 from PPG Industries (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Silicone L-71 1, L-720, L-721 and L722 (dimethicone copolyols from Union Carbide); Silicone L-7000, L-7001, L-7002, L-7004, L-7500, L-7600, L-7602, L-7604, L-7605, and L-7610 (dimethicone copolyols from Union Carbide); Unisil SF-R (dimethiconol from UPI); Silicate Cluster from Olin (Tris[tributoxysiloxy]methylsilane); Siloplane Fluids (available from Chisso Corp.) silicone copolymer F-754 (dimethicone copoly from SWS Silicones); Silwaxes from Siltech; Wacker Silicone Fluid L Series (available from Wacker Silicone) and combinations thereof.

Other nonlimiting examples of suitable nonvolatile silicones include those described in WO 7/16162 and WO 97/16161, both published on May 9, 1997, and both descriptions being incorporated by reference herein.

Other mitigating materials, although less preferred, are non-silicone containing organic emollients including petrolatum, lanolin, acetylated lanolin, hydroxylated lanolin, sucrose polyesters, cholesterol hydroxy stearate, and combinations thereof. Among the non-silicone containing emollients, highly occlusive materials such as petrolatum are most preferred.

V. Optional Carriers

The antiperspirant and deodorant compositions of the present invention may further comprise one or more carriers in addition to the mitigating materials and volatile, nonpolar hydrocarbon liquids described hereinbefore.

Preferred optional carriers are volatile silicone carriers. These volatile silicones will typically have a viscosity as measured at 25° C. of less than about 10 centistokes, and may have cyclic, linear or branched configurations, nonlimiting examples of which are described in Todd et al., "Volatile Silicone Fluids for Cosmetics", Cosmetics and Toiletries, 91:27–32 (1976), which descriptions are incorporated herein by reference.

The optional volatile silicone carrier is preferably a cyclic silicone, and preferably has from about 3 to about 7, more preferably from about 4 to about 5, silicon atoms. Most preferably are those volatile cyclic silicones which conform to the formula:

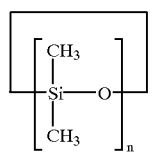

wherein n is from about 3 to about 7, preferably from about 4 to about 5, most preferably 5 (cyclopentasiloxane). Suitable volatile silicones for use herein include, but are not limited to, cyclopentasiloxane (commercially available from G. E. Silicones); Dow Corning 244 and Dow Corning 245 (commercially available from Dow Corning Corp.); GE 7207, GE 7158 and Silicone Fluids SF-1202 and SF-1 173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V ( available from Mazer) and combinations thereof.

The optional liquid carrier may comprise other polar or non-polar, volatile or nonvolatile, organic or nonorganic carriers, carrier material that is known for use in antiperspirant/deodorant or other personal care product, or which is otherwise safe and effective for topical application to human skin, other than the volatile, nonpolar hydrocarbon liquid and irritation-mitigating materials described herein. Examples of such other optional liquid carriers include those described in U.S. Pat. No. 5,750,096 (Guskey); U.S. Pat. No. 5,733,534 (Sawin et al.); U.S. Pat. No. 5,718,890 (Putman et al.); U.S. Pat. No. 5,429,816 (Hofrichter et al.); U.S. Pat. No. 5,605,681 (Trandai et al.); and U.S. Pat. No. 5,585,092 (Trandai et al.), which descriptions are incorporated herein by reference.

VI. Suspending or Thickening Agent

The antiperspirant and deodorant compositions of the present invention may further comprise a suspending or thickening agent to help provide the composition with the desired viscosity, rheology, texture or product hardness, or to otherwise help suspend any dispersed solids or liquids within the composition. The terms "suspending agent" and "thickening agent" are used interchangeably herein and include any material known or otherwise effective in providing suspending, gelling, viscosifying, solidifying or thickening properties to the composition or which otherwise provide structure to the final product form. These suspending or thickening agents include gelling agents, and polymeric or nonpolymeric or inorganic thickening or viscosifying agents. Such materials will most typically include organic solids, silicone solids other than the silicone mitigating materials described herein, crystalline or other gellants, inorganic particulates such as clays or silicas, or combinations thereof.

The concentration and type of the optional suspending or thickening agent selected for use in the antiperspirant composition will vary depending upon the desired product form, viscosity, and hardness. For most suspending or thickening agents suitable for optional use herein, the concentration of such suspending or thickening agents will most typically range from about 0.1% to about 35%, more typically from about 0.1% to about 20%, by weight of the composition.

Suitable gelling agents for use as optional suspending or thickening agents in the antiperspirant or deodorant compositions include, but are not limited to, fatty acid gellants, salts of fatty acids, hydroxy acids, hydroxy acid gellants, esters and amides of fatty acid or hydroxy fatty acid gellants, cholesterolic materials, dibenzylidene alditols, lanolinolic materials, fatty alcohols, triglycerides, sucrose esters such SEFA behenate, inorganic materials such as clays or silicas, and other amide or polyamide gellants.

Suitable gelling agents include fatty alcohols having from about 8 to about 40 carbon atoms, preferably from 8 to about 30 carbon atoms, more preferably from about 12 to about 18 carbon atoms. These gelling agents are wax-like materials which are most typically used at concentrations ranging from about 1% to about 25%, preferably from about 5% to about 20%, most preferably from about 10% to about 20%, by weight of the antiperspirant composition. Preferred are cetyl alcohol, myristyl alcohol, stearyl alcohol and combinations thereof, more preferably stearyl alcohol.

Other suitable gelling agents include waxes or wax-like materials having a melt point of above 65° C., more typically from about 65° C. to about 130° C., examples of which include, but are not limited to, waxes such as beeswax, carnauba, baysberry, candelilla, montan, ozokerite, ceresin, hydrogenated castor oil (castor wax), synthetic waxes, microcrystalline waxes. Castor wax is preferred within this group. Other high melting point waxes are described in U.S. Pat. No. 4,049,792, Elsnau, issued Sep. 20, 1977, which description is incorporated herein by reference.

Other suitable gelling agents include fatty acid gellants such as fatty acid and hydroxy or alpha hydroxy fatty acids, having from about 10 to about 40 carbon atoms, and esters and amides of such gelling agents. Non-limiting examples such gelling agents include 12-hydroxystearic acid, 12-hydroxylauric acid, 1 6-hydroxyhexadecanoic acid, behenic acid, eurcic acid, stearic acid, caprylic acid, lauric acid, isostearic acid, and combinations thereof. Preferred are 12-hydroxystearic acid, esters of 12-hydroxystearic acid, amides of 12-hydroxystearic acid and combinations thereof, and all other gelling agents which correspond to the following formula:

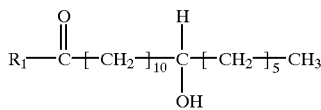

wherein $R_1$ is $OR_2$, $NR_2R_3$, or a silicone containing moiety; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and combinations thereof. Most preferred is 12-hydroxystearic acid.

Suitable amide gellants include disubstituted or branched monoamide gellants, monosubstituted or branched diamide gellants, triamide gellants, and combinations thereof, including n-acyl amino acid derivatives such as n-acyl amino acid amides, n-acyl amino acid esters prepared from glutamic acid, lysine, glutamine, apartic acid, and combinations thereof. Other suitable amide gelling agents are described in U.S. Pat. No. 5,429,816, issued Jul. 4, 1995, and U.S. patent application Ser. No. 081771,183, filed Dec. 20, 1996, which descriptions are incorporated herein by reference. Concentrations of all such gelling agents preferably range from about 0.1 % to about 25%, preferably of from about 1% to about 15%, more preferably from about 1% to about 10%, by weight of the antiperspirant composition.

Other suitable gelling agents include triglyceride gellant systems which comprise glyceryl tribehenate and other triglycerides, wherein at least about 75%, preferably about 100%, of the esterified fatty acid moieties of said other triglycerides each have from about 18 to about 36 carbon atoms, and wherein the molar ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gellant material preferably has a melting point of at less than about 110° C., preferably between about 50° C. and 110° C.

Preferred concentrations of the above-described triglyceride gellant systems range from about 0.1% to about 20%, more preferably from about 0.5% to about 15%, by weight of the antiperspirant composition. For roll-on formulations having a penetration force value of from about 20 gram-.force to about 100 gram.force, triglyceride concentrations preferably range from about 1% to about 5% by weight of the antiperspirant composition. For other cream formulations, including those formulations suitable for use in cream applicator devices, which have a penetration force value of from about 100 gram.force to about 500 gram.force, triglyceride concentrations preferably range from about 4% to about 20%, more preferably from about 4% to about 10%, by weight of the antiperspirant composition.

Specific examples of triglyceride gelling agents for use in the antiperspirant compositions that are commercially available include, but are not limited to, tristearin, hydrogenated vegetable oil, trihydroxysterin (Thixcin® R, available from Rheox, Inc.), rape seed oil, castor wax, fish oils, tripalmhitin, Syncrowax® HRC and Syncrowax® HGL-C (Syncrowax® available from Croda, Inc.).

Other suitable suspending or thickening agents for use in the antiperspirant and deodorant compositions include particulate suspending or thickening agents such as clays and colloidal pyrogenic silica pigments. Other known or otherwise effective particulate suspending or thickening agents can likewise be used in the antiperspirant composition. Concentrations of optional particulate thickening agents preferably range from about 0.1% to about 15%, more preferably from about 1% to about 15%, even more preferably from about 1% to about 8%, by weight of the composition. Colloidal pyrogenic silica pigments are preferred, a common example of which includes Cab-O-Sil®, a submicroscopic particulated pyrogenic silica.

Suitable clay suspending or thickening agents include montmorillonite clays, examples of which include bentonites, hectorites, and colloidal magnesium aluminum silicates. These and other suitable clay suspending agents are preferably hydrophobically treated, and when so treated will generally be used in combination with a clay activator. Non-limiting examples of suitable clay activators include propylene carbonate, ethanol, and combinations thereof. The amount of clay activator will typically range from about 25% to about 75% by weight of the clay, more typically from about 40% to about 60% by weight of the clay.

Preferred thickening or gelling agents for the deodorant embodiments of the present invention are the salts of fatty acids, wherein the fatty acid moiety has from about 12 to about 40 carbon atoms, preferably from about 12 to about 22 carbon atoms, more preferably from about 16 to about 20 carbon atoms, most preferably about 18 carbon atoms.

Suitable salt forming cations for use with these gelling agents include metal salts such as alkali metals, e.g. sodium and potassium, and alkaline earth metals, e.g. magnesium, and aluminum. Preferred are sodium and potassium salts, more preferably sodium stearate, sodium palmitate, potassium stearate, potassium palmitate, sodium myristate, aluminum monostearate, and combinations thereof. Most preferred is sodium stearate.

VII. Other Optional Materials

The antiperspirant and deodorant compositions of the present invention may further comprise one or more other optional materials that are known for use in antiperspirant, deodorant or other personal care product, or which is otherwise suitable for topical application to human skin.

Nonlimiting examples of such other optional materials include dyes or colorants, emulsifiers, perfumes, distributing agents, pharmaceutical or other topical active, preservatives, surfactants, processing aides such as viscosity modifiers, wash-off aids, and so forth. Examples of such optional materials are described in U.S. Pat. No. 4,049,792, Elsnau, issued Sep. 20, 1977; U.S. Pat. No. 5,019,375, Tanner et al., issued May 28, 1991; and U.S. Pat. No. 5,429,816, Hofrichter et al., issued Jul. 4, 1995; which descriptions are incorporated herein by reference.

The antiperspirant embodiments of the present invention preferably comprise a combination of volatile and nonvolatile silicone materials as described in U.S. Pat. No. 5,156,834 (Beckmeyer et al). Such embodiments can be formulated into any product form, e.g., solid, liquid, semi-solid.

VIII. Product Form

The antiperspirant and deodorant compositions of the present invention can be formulated as any known or otherwise effective product form for providing topical application of antiperspirant or deodorant active to the desired area of the skin. Nonlimiting examples of such product forms include liquids, solids (gel solids, solid sticks, suspensoids) and soft solids/creams/semi-solids, lotions, aerosols and nonaerosol sprays, roll-ons and so forth.

The antiperspirant embodiments of the present invention are preferably in the form of a soft solids or creams, and more preferably a soft solid or cream containing the materials described or otherwise claimed in U.S. Pat. No. 5,156,834 (Beckmeyer et al.) and/or U.S. Pat. No. 5,718,890 (Putman et al.), which descriptions are incorporated herein by reference. All antiperspirant embodiments of the present invention, regardless of product form, preferably contain the combination of volatile and nonvolatile silicones as described in U.S. Pat. No. 5,156,834 (Beckmeyer et al.).

IX. Methods of Manufacture

The antiperspirant and deodorant compositions of the present invention may be prepared by any known or otherwise effective technique, suitable for providing an antiperspirant or deodorant composition of the desired form and having the essential materials described herein. Many such techniques are described in the antiperspirant and formulation arts for each of the described product forms.

X. Method of Use

The antiperspirant and deodorant compositions may be applied topically to the axilla or other area of the skin in an amount effective to treat or reduce perspiration wetness and/or malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied to the axilla or other area of the skin, one or two times daily, preferably once daily, to achieve effective antiperspirant and/or malodor control over an extended period.

XI. EXAMPLES

The following non-limiting examples illustrate specific antiperspirant and deodorant embodiments of the present invention, including non-limiting examples of methods of manufacture and use. Each of the exemplified compositions are prepared by methods well known in the formulation art for preparing the various antiperspirant and deodorant product forms. All exemplified amounts are weight percents based on the total weight of the antiperspirant or deodorant composition, unless otherwise specified.

Examples 1–7

The compositions described in Table 1 are antiperspirant compositions in the form of soft solids/semisolids/creams. These exemplified compositions can be prepared by methods well known in the art for preparing such product forms, examples of such methods including those described in U.S. Pat. No. 5,718,890 (Putman et al.) and U.S. Ser. No.08/738,631 (Bretzler et al.), which descriptions are incorporated herein by reference.

TABLE 1

| Antiperspirant Soft Solids/Semisolids/Creams | | | | | | | |
|---|---|---|---|---|---|---|---|
| Ingredient | Example 1 | Example 2 | Example 3 | Example 4 | Example 5 | Example 6 | Example 7 |
| Al Zr trichlorohydrex glycinate | 25.25 | 25.25 | 25.25 | 25.25 | 25.25 | 25.25 | 25.25 |
| Isohexadecane | — | — | — | — | 20 | — | — |
| C13–C14 Isoparaffin | 10 | 10 | 10 | 20 | — | 8 | 10 |
| Cyclopentasiloxane | 52.75 | 52.75 | 40.75 | 42.75 | 42.75 | 39.75 | 40.75 |
| Tribehenin | 5.0 | 5.0 | — | 5.0 | 5.0 | — | — |
| Petrolatum | — | 5.0 | — | — | — | — | 5.0 |
| Dimthicone 50 cs | — | — | — | 5.0 | — | — | — |
| Dimethicone 10 cs | 5.0 | — | 5.0 | — | 5.0 | 8.0 | — |
| C18–36 Acid Triglyceride | 1.25 | 1.25 | — | 1.25 | 1.25 | — | — |
| Perfume | 0.75 | 0.75 | — | 0.75 | 0.75 | — | — |
| Hydrogenated caster oil | — | — | 6.0 | — | — | 6.0 | 6.0 |
| Talc | — | — | 6.0 | — | — | 6.0 | 6.0 |
| Silicone wax GE SF1642 | — | — | 6.0 | — | — | 6.0 | 6.0 |
| Bentone | — | — | 1.0 | — | — | 1.0 | 1.0 |

Examples 8–12

The compositions described in Table 2 are antiperspirant compositions in the form of solid sticks. These exemplified compositions can be prepared by methods well known in the art for preparing such product forms, examples of such methods including those described in U.S. Pat. No. 4,985,238 (Tanner et al.), which descriptions are incorporated herein by reference.

Examples 19–23

The compositions described in Table 4 are antiperspirant compositions in the form of gel solid sticks. These compositions contain gellants as suspending agents, wherein the suspending agents contain polar functional groups (e.g., carboxylic acid, amide). The selected suspending agents are 12-hydroxystearic acid and N-lauryl-glutamic acid-di-n-butyl amide. Each of these exemplified compositions described in Table 4 are prepared by methods well known in the art for preparing such product forms, examples of such methods including those described in U.S. Pat. No. 5,429,816 (Hofrichter et al.), which descriptions are incorporated herein by reference.

TABLE 2

Solid Antiperspirant Sticks

| Ingredient | Example 8 | Example 9 | Example 10 | Example 11 | Example 12 |
|---|---|---|---|---|---|
| Cyclopentasiloxane | 37.635 | 32.635 | 37.635 | 37.635 | 41.135 |
| Al Zr trichlorohydrex glyCinate | 20 | 20 | 20 | 20 | 20 |
| Stearyl alcohol | 12.5 | 12.5 | 12.5 | 12.5 | 11.0 |
| Talc | 11.0 | 11.0 | 11.0 | 11.0 | 11.0 |
| C13–C14 Isoparaffin | 10 | 15 | 10 | 10 | 10 |
| Petrolatum | — | — | — | 5.0 | — |
| Silicone wax | — | — | 5.0 | — | — |
| Dimethicone 50 cs | 5.0 | 5.0 | — | — | 3.0 |
| Hydrogenated castor oil | 2.9 | 2.9 | 2.9 | 2.9 | 2.9 |
| Perfume | 0.35 | 0.35 | 0.35 | 0.35 | 0.35 |
| Silica | 0.18 | 0.18 | 0.18 | 0.18 | 0.18 |
| Dipropylene glycol | 0.18 | 0.18 | 0.18 | 0.18 | 0.18 |
| Polyethylene | 0.18 | 0.18 | 0.18 | 0.18 | 0.18 |
| Behenyl alcohol | 0.075 | 0.075 | 0.075 | 0.075 | 0.075 |

Examples 13–18

The compositions described in Table 3 are antiperspirant compositions in the form of aerosols and roll-on liquids. Each of these exemplified compositions can be prepared by methods well known in the art for preparing such product forms, examples of such methods including those described in U.S. Pat. No. 4,904,463 (Johnson et al.) and U.S. Pat. No. 5,298,236 (Orr et al.), which descriptions are incorporated herein by reference.

TABLE 3

Liquid Antiperspirant Roll-ons and Aerosols

| Ingredient | Example 13 (roll-on) | Example 14 (roll-on) | Example 15 (roll-on) | Example 16 (aerosol) | Example 17 (aerosol) | Example 18 (aerosol) |
|---|---|---|---|---|---|---|
| C13–C14 Isoparaffin | 23.03 | 23.03 | 13.03 | 5.00 | 5.00 | 6.00 |
| Cyclopentasiloxane | 20.00 | 20.00 | 20.00 | 11.37 | 13.37 | 13.37 |
| Dimethiconol 80 cs | 10.00 | — | — | — | — | — |
| Dimethicone 50 cs | — | 20.10 | 10.00 | 5.00 | 3.00 | 2.00 |
| Mineral oil | 10.10 | — | 20.10 | — | — | — |
| Al Zr trichlorohydrex gly. | 25.13 | 25.13 | 25.13 | — | — | — |
| Quaternium-18 Hectorite HL | 4.02 | 4.02 | 4.02 | 1.00 | 1.00 | 1.00 |
| Propylene carbonate | 0.99 | 0.99 | 0.99 | 0.33 | 0.33 | 0.33 |
| Dipropylene glycol | 0.90 | 0.90 | 0.90 | — | — | — |
| Polyethylene powder | 5.53 | 5.53 | 5.53 | — | — | — |
| Al chlorohydrate | — | — | — | 12.00 | 12.00 | 12.00 |
| Propellant | — | — | — | 60.00 | 60.00 | 60.00 |
| Isopropyl myristate | — | — | — | 5.00 | 5.00 | 5.00 |
| Perfume | 0.30 | 0.30 | 0.30 | 0.30 | 0.30 | 0.30 |

TABLE 4

Gel Solid Antiperspirant Sticks

| Ingredient | Example 19 | Example 20 | Example 21 | Example 22 | Example 23 |
|---|---|---|---|---|---|
| C13–C15 Isoparaffins | 30 | 26 | 26 | — | 25 |
| C14–C18 Isoparaffins | — | — | — | 26 | — |
| Cyclopentasiloxane | 21.8 | — | 9.8 | 9.8 | 12.3 |

TABLE 4-continued

Gel Solid Antiperspirant Sticks

| Ingredient | Example 19 | Example 20 | Example 21 | Example 22 | Example 23 |
|---|---|---|---|---|---|
| Dimethiconol 80 cs | 10 | 36.55 | 26 | 26 | 26 |
| 12-Hydroxystearic Acid | 7 | 7 | 7 | 7 | 7 |
| N-Lauryl-Glutamic acid-di-n-butyl amide | 2 | 2 | 2 | 2 | 2 |
| Dipropylene Glycol | 1 | 0.25 | — | — | — |
| Tripropylene Glycol | — | — | 1 | 1 | — |
| Octyldodecanol | 1 | 1 | 1 | 1 | — |
| Ceteareth-20 | 0.5 | 0.5 | 0.5 | 0.5 | — |
| Unilin 425 | 0.5 | 0.5 | 0.5 | 0.5 | 0.5 |
| Al/Zr trichlorohydrex gly. | 25 | 25 | 25 | 25 | 25 |
| Disodium EDTA | 0.2 | 0.2 | 0.2 | 0.2 | 0.2 |
| Perfume | 1 | 1 | 1 | 1 | 1 |

Examples 24–25

The compositions described in Table 5 are deodorant stick compositions. Each of these exemplified compositions can be prepared by methods well known in the art for preparing such product forms, examples of such methods including those described in U.S. Pat. No. 5,605,681 (Trandai et al.) and U.S. Pat. No. 5,585,092 (Trandai et al.), which descriptions are incorporated herein by reference.

TABLE 5

Gel Deodorant Sticks

| Ingredient | Example 24 | Example 25 |
|---|---|---|
| C11–C13 Isoparaffin | — | 17.0 |
| C13–C14 Isoparaffin | 34.0 | 17 |
| Triclosan | 0.3 | 0.3 |
| Hexylene glycol | 15.0 | 15.0 |
| PEG-8 | 22.575 | 22.575 |
| glycerin | 5.0 | 5.0 |
| Sodium stearate | 5.6 | 5.6 |
| EDTA | 0.025 | 0.025 |
| Sodium hydroxide | 0.50 | 0.50 |
| Dimethicone 50 cs | 12.0 | 12.0 |
| Perfume | 3.5 | 3.5 |
| Dye solution | 1.5 | 1.5 |

Examples 26–27

The compositions described in Table 6 are antiperspirant suspensions/emulsions. Each of these exemplified compositions can be prepared by methods well known in the art for antiperspirant emulsion compositions.

TABLE 6

Antiperspirant Emulsion

| Ingredient | Example 26 Aqueous Emulsion | Example 27 Anhydrous Emulsion |
|---|---|---|
| Zirconium aluminum glycinate as 50% aqueous solution | 50.0 | — |
| hexylene glycol | 12.0 | — |
| PEG-8 | 10.0 | — |
| water | 13.0 | — |
| perfume | 1.0 | 1.0 |
| dimethicone 50 cs | 2.0 | 5.0 |
| Abil WE09 | 1.0 | — |
| Silicone gum as 25% gum in cylopentasiloxane | 1.0 | — |
| dimethicone copolyol | 5.0 | — |
| DC3225 | | |
| Isopar M | 5.0 | 5.0 |
| Abil EM90 | — | 4.0 |
| Zirconium aluminum glycinate as 30% active in propylene glycol | — | 50.0 |
| Tripropylene glycol | — | 35.0 |

The compositions as described in Tables 1–6 (Examples 1–27) are applied topically to the axilla once or twice daily in an amount sufficient to provide the desired antiperspirant and/or deodorant efficacy, and are applied topically in accordance with the methods described herein. The applied compositions have a dry skin feel during and after application and cause minimal or no skin irritation.

XII. Skin Irritation Data

The antiperspirant/deodorant compositions described in Table 7 are tested for skin irritation by a standard 7-day cumulative patch test. The patch test results are also set forth in Table 7.

TABLE 7

Cumulative 7-day Skin Irritation Study

| Ingredient | Example 28 | Example 29 | Example 30 | Example 31 |
|---|---|---|---|---|
| Al Zr glycinate | 25.25 | 25.25 | 25.25 | 25.25 |
| C13–C14 Isoparaffin | — | 10 | 20 | 20 |
| Cyclopentasiloxane | 62.75 | 52.75 | 42.75 | 47.75 |
| Tribehenin | 5.0 | 5.0 | 5.0 | 5.0 |
| C18–C36 Acid triglyceride | 1.25 | 1.25 | 1.25 | 1.25 |
| Dimethicone 10 cs | 5.0 | 5.0 | 5.0 | — |
| Perfume | 0.75 | 0.75 | 0.75 | 0.75 |
| LS mean grade ± 0.037 std error | 0.0279 | 0.607 | 0.899 | 1.159 |
| Irritation | low | low | low | high |

The formulations identified as Examples 28–31 in Table 7 are evaluated for skin-irritation potential in human subjects according to a 7-day cumulative patch test protocol. This test is well known and commonly used in the industry to assess materials and products for skin irritation potential. Each of the test samples (Examples 28–31) is applied to the outer upper aspect of either the right and/or left arm(s) or back, under occlusive conditions for 7 days, 23 hour periods. There is a minimum of 30 subjects for each test sample. Patches are removed from each subject at approximately 23 hours after patch application daily and a new patch applied after the application site has been graded for irritation. Patch sites are graded approximately one hour following removal of each patch daily. Patch sites are graded and an LS mean grade calculated for each sample. Skin irritation grades are based upon the following 0–4 scale described in Table 8.

TABLE 8

Skin Irritation Patch Test Grading

| | |
|---|---|
| 0 | No apparent cutaneous involvement |
| 0.5 | Greater than 0, less than 1 (e.g., faint, barely perceptible erythema or slight dryness (glazed appearance)) |
| 1 | Faint but definite erythema, no eruptions or broken skin or no erythema but definite dryness; may have epidermal fissuring |
| 1.5 | Greater than 1, less than 2 (e.g., well-defined erythema or faint erythema with definite dryness, may have epidermal fissuring) |
| 2.0 | Moderate erythema, may have a few papules or deep fissures, moderate-to-serve erythema in the cracks Cut-off grade- patches are not re-applied. |
| 2.5 | Greater than 2, less than 3 (e.g., moderate erythema with barely perceptible edema or severe erythema not involving a significant portion of the patch (halo effect around the edges), may have a few papules or moderate-to-severe erythema) |
| 3.0 | Severe erythema (beet redness), may have generalized papules or moderate-to-severe erythema with slight edema (edges well defined by raising). |
| 3.5 | Greater than 3, less than 4 (e.g., moderate-to-severe erythema with moderate edema (confined to patch area) or moderate-to-severe erythema with isolated eschar formations or vesicles) |
| 4.0 | Generalized vesicles or eschar formations or moderate-to severe erythema and/or edema extending beyond the area of the patch. |

The data as set forth in Table 7 show that volatile, nonpolar hydrocarbon liquids (e.g., C13–C14 Isoparaffin) are irritating when applied to the skin from an antiperspirant/deodorant composition (Example 31—LS mean grade 1.159±0.037) and that mitigating materials (e.g., dimethicone 10 cs) can be used to reduce or eliminate the skin irritation from such compositions (Examples 28–30—LS mean grades of 0.279, 0.607, 0.899, all ±0.037). As shown in Table 7, the skin irritation grades from Examples 28–30 which contain a mitigating material are all less than the skin irritation grade for Example 31 which contains no mitigating material.

What is claimed is:

1. A antiperspirant/deodorant composition comprising:
   (a) from about 0.01% to about 60% by weight of an antiperspirant/deodorant active selected from the group consisting of antiperspirant active, deodorant active, perfumes, and combinations thereof;
   (b) from about 1% to about 60% by weight of a volatile, nonpolar hydrocarbon liquid having a solubility parameter of less than about 7.5 $(cal/cm^3)^{0.5}$ and a vapor pressure as measured at 25° C. of from about 0.01 mmHg to about 6.0 mmHg; and
   (c) from about 1% to about 60% by weight of a mitigating material having a vapor pressure equal to or less than the vapor pressure of the volatile, nonpolar hydrocarbon liquid;
wherein the weight ratio of the volatile, nonpolar hydrocarbon liquid to the mitigating material is from about 5:1 to about 1:50.

2. The composition of claim 1 wherein the active is an antiperspirant active comprising an aluminum salt.

3. The composition of claim 2 wherein the composition comprises from about 5% to about 35% by weight of an aluminum zirconium polymer as an antiperspirant active.

4. The composition of claim 1 wherein the composition comprises a deodorant active selected from the group consisting of antimicrobial agents, deodorant perfumes, malodor-absorbing materials, and combinations thereof.

5. The composition of claim 4 wherein the composition comprises from about 0.01% to about 10% by weight of an antimicrobial agent.

6. The composition of claim 5 wherein the composition comprises from about 0.01% to about 1.0% by weight of an antimicrobial agent selected from the group consisting of triclosan, triclocarban and combinations thereof.

7. The composition of claim 1 wherein the composition comprises from about 5% to about 30% by weight of the mitigating material.

8. The composition of claim 1 wherein weight ratio of the volatile, nonpolar hydrocarbon liquid to the mitigating material is from about 3:1 to about 1:5.

9. The composition of claim 1 wherein the mitigating material is nonvolatile silicone.

10. The composition of claim 9 wherein the nonvolatile silicone is a silicone liquid selected from the group consisting of a polydimethylsiloxane, dimethiconol, and combinations thereof.

11. The composition of claim 10 wherein nonvolatile silicone liquid is a polydimethylsiloxane having a viscosity as measured at 25° C. of from about 5 centistokes to about 1,000 centistokes.

12. The composition of claim 1 wherein the volatile, nonpolar hydrocarbon liquid is a branched chain hydrocarbon having from about 4 to about 40 carbons atoms.

13. The composition of claim 12 wherein the volatile branched chain hydrocarbon has a solubility parameter of from about 5.0 to about 7.5 $(cal/cm^3)^{0.5}$ and a vapor pressure of from about 0.01 mmHg to about 2.0 mmHg at 25° C.

14. The composition of 12 wherein the volatile, nonpolar hydrocarbon liquid is selected from the group consisting of isododecane, isohexadecane, isoeicosane, and combinations thereof.

15. The composition of claim 13 wherein the composition comprises a combination of two or more volatile branched chain hydrocarbons having different molecular weights, each of which also has from about 6 to about 20 carbon atoms.

16. The composition of claim 15 wherein the volatile branched chain hydrocarbon is selected from the group consisting of C13–C14 Isoparaffin, C7–C8 Isoparaffin, C8–C9 Isoparaffin, C10–11 Isoparaffin, C11–C13 Isoparaffin, C11–C12 Isoparaffin, C14–C18 Isoparaffins, and combinations thereof.

17. The composition of claim 1 wherein the composition further comprises a volatile silicone which conforms to the formula:

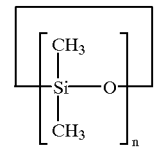

wherein n is from about 3 to about 7.

18. The composition of claim 1 wherein the mitigating material comprises a non-silicone emollient selected from the group consisting of petrolatum, glycerin, sucrose polyesters, and combinations thereof.

19. The composition of claim 1 wherein the composition further comprises from about 0.1% to about 35% by weight of a suspending agent.

20. The composition of claim 19 wherein the composition is a deodorant composition comprising from about 0.1% to about 35% of a C12 to C40 fatty acid salt as a suspending agent.

21. The composition of claim 20 wherein the fatty acid salt is sodium stearate.

22. The composition of claim 9 wherein the composition further comprises a volatile silicone.

23. The composition of claim 1 wherein the composition is in the form of a semisolid.

24. The composition of claim 1 wherein the composition is in the form of an aerosol spray.

25. The composition of claim 1 wherein the composition is in the form of a solid stick.

26. The composition of claim 19 wherein the suspending agent contains a polar functionality and the mitigating material is a polyalkyl silanol siloxane.

27. The composition of claim 26 wherein the suspending agent is selected from the group consisting of suspending agents containing at least one carboxylic acid functionality, suspending agents containing at least one amide functionality, and combinations thereof, and the mitigating material polyalkyl silanol siloxane is dimethiconol.

28. The composition of claim 27 wherein the dimethiconol has a silanol content of from about 0.1% to about 5.0% silanol and a viscosity of from about 20 centistokes to about 1000 centistokes.

29. The composition of claim 28 wherein the dimethiconol has a viscosity of from about 20 centistokes to about 100 centistokes.

30. The composition of claim 29 wherein the suspending agent comprises 12-hydroxystearic acid.

31. A method for treating or reducing perspiration wetness and malodor, comprising applying from about 0.1 gram to about 20 grams of the composition of claim 2 to the desired area of the skin.

32. A method for treating or reducing perspiration wetness malodor, comprising applying from about 0.1 gram to about 20 grams of the deodorant composition of claim 4 to the desired area of the skin.

33. A method for topically applying an antiperspirant composition containing a volatile, nonpolar hydrocarbon liquid to minimize skin irritation, said method comprises the application of from about 0.1 gram to about 20 grams of the composition of claim 2.

34. A method for topically applying a deodorant composition containing a volatile, nonpolar hydrocarbon liquid to minimize skin irritation, said method comprises the application of from about 0.1 gram to about 20 grams of the composition of claim 4.

* * * * *